United States Patent [19]

Llobet et al.

[11] Patent Number: 4,689,346
[45] Date of Patent: Aug. 25, 1987

[54] THERAPEUTIC 1-(ACYLAMINO)-NAPHTHALENE-4-SULPHONIC ACID DERIVATIVES

[75] Inventors: Pere P. Llobet; Elisa G. Baylina, both of Barcelona, Spain

[73] Assignee: Laboratorio Fides, S.A., Spain

[21] Appl. No.: 791,934

[22] Filed: Oct. 28, 1985

Related U.S. Application Data

[63] Continuation of Ser. No. 538,959, Oct. 4, 1983, abandoned.

[30] Foreign Application Priority Data

Oct. 6, 1982 [ES] Spain ..................... 516248

[51] Int. Cl.$^4$ .................... A61K 00/00; C07C 143/00
[52] U.S. Cl. ................. 514/555; 260/501.12; 260/501.21; 260/507 R; 560/139; 544/110; 546/348
[58] Field of Search .......... 260/507 R, 501.21, 501.12; 544/110; 560/139; 514/555

[56] References Cited

PUBLICATIONS

Roskam, E. R., Soc. Biol., (Brit.), 122, 1245–1250, (1933).
Roskam et al., Archs. Int. Pharmocodyn. Ther., 57, 450–466, (1937).
Astrup et al., Arch. Biochem., 40, 346–351, (1952).
Lefebvre et al., Societe Belge De Biologie, Seance Du 27 Janvier 1962, pp. 183–186.
Elsevier's Encyclopedia of Organic Chemistry, Ed. F. Radt, vol. 12B, 1955, pp. 5049–5050 & 5401–5402.
Barco et al., Chem. Abstr., 82, 111705n, (1974).
Horyna et al., Ibid, 97, 199538n, (1982).
Horyna, Ibid, 94, 67284e, (1980).

Primary Examiner—Nicky Chan
Attorney, Agent, or Firm—Steinberg & Raskin

[57] ABSTRACT

Compounds for effecting hemostatic and antifibrinolytic action, namely a 1-acylamino naphthalene-4 sulphonic acid derivative of the formula

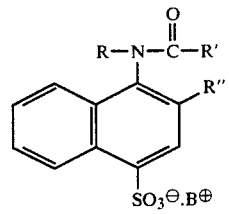

and compositions and method of achieving such action.

7 Claims, No Drawings

THERAPEUTIC 1-(ACYLAMINO)-NAPHTHALENE-4-SULPHONIC ACID DERIVATIVES

This is a continuation of application Ser. No. 538,959, filed 10/4/83, abandoned.

BACKGROUND OF THE INVENTION

The present invention relates to therapeutically useful 1-(acylamino)-naphthalene-4-sulphonic acid derivatives, to processes for obtaining the said derivatives, to the formulation of pharmaceutical compositions for use in therapeutics, and to methods for achieving the therapeutic benefits. Preferred embodiments are derivatives of low toxicity having a hemolytic and antifibrinolytic activity and affecting capillary permeability and resistance.

SUMMARY OF THE INVENTION

The derivatives according to the present invention have the following general formula I:

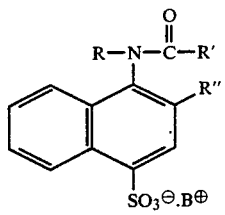

Formula I wherein R is hydrogen or a lower alkanoyl radical; R' is a lower alkyl radical; R" is hydrogen, a hydroxy or lower alkanoyloxy radical; and B+ is a cation of an alkali metal, an alkaline earth metal or a compound containing a basic nitrogen atom and being selected from the group consisting of pyridine, morpholine, diethylamine, tranexamic acid (trans-4-(aminomethyl)-cyclohexanecarboxylic acid=AMCHA), ε-aminocaproic acid (EACA) and p-aminomethylbenzoic acid (PAMBA).

One or more of the compounds may be administered orally, parenterally, or topically, the parenteral route being preferred.

In pharmaceutical compositions these compounds may be accompanied by suitable excipients. The pharmaceutical forms for oral administration may be capsules, tablets, sugar-coated pills, syrups, solutions or suspensions. The daily dosage used in oral application may be 10 mg to 150 mg of the active compound per kg of body weight, administered in various doses.

The compound(s) may be combined with other therapeutic agents depending on the specific circumstances of the illness being treated.

A derivative according to the invention may be obtained by a process in which a corresponding 1-amino-2-naphthol-4-sulphonic acid or 1-amino-4-naphthalene-sulphonic acid is acylated by means of a lower alkanoyl chloride or the corresponding anhydride (preferably acetic anhydride), in the presence of a tertiary amine (preferably pyridine or triethylamine) or a salt such as potassium acetate, so as to obtain respectively the pyridine, triethylamine, or potassium salt. The formation of monoacylated, diacylated or triacylated products depends on the proportion of acylating agent employed and the reaction conditions. If it is desired to convert the product to a different salt (i.e. to change the cation), this may be effected by reaction with a compound selected from: hydrochlorides of amines and amino acids; alkali metal bi-tartrates; the aforementioned amines and amino acids; or the perchlorate of a desired alkaline earth metal. Similarly, the salts may be obtained by direct reaction of the free acids of the previously obtained naphthalenesulphonic derivatives with the various amines and amino acids or with the hydroxides and carbonates of the corresponding metals. The monoacylated and diacylated compounds may be obtained by hydrolysis of their analogues having a higher degree of acylation.

DESCRIPTION OF PREFERRED EMBODIMENTS

Various examples of obtaining new naphthalenesulphonic acid derivatives of the general formula I will be described hereinafter.

EXAMPLE 1

A mixture of 10 g (0.04 mole) of 1-amino-2-naphthol-4-sulphonic acid, 10 g of potassium acetate and 100 ml of acetic anhydride is heated to boiling until the solids have completely dissolved; the mixture is cooled to 3° C. and after 6 hours, the precipitate obtained is filtered and washed with diethyl ether. When dry, the compound is recrystallized in ethanol/water, 11 g (Yield 74%) of potassium N,N,O-triacetyl-1-amino-2-naphthol-4-sulphonate being obtained, which has a melting point (m.p.) of 258°–260° C. and whose IR spectrum (KBr) has the following bands: 3,450; 1,755; 1,700; 1,310; 1,200; 1,040; 1,000; 990, 750; 640; 610.

NMR ($D_2O$) δ 8.6–7.3 (m, aromatic), δ 2.3 (s, $OCOCH_3$), δ 2.2 (s, $CH_3-CO-N-CO-CH_3$).

EXAMPLE 2

60 g (0.16 mole) of potassium N,N,O-triacetyl-1-amino-2-naphthol-4-sulphonate dissolved in the minimum amount of water is placed in a flask provided with a stirrer, and an aqueous solution containing 20.5 g of morpholine hydrochloride (0.16 mole) is then added. The resultant solution is heated for 15 minutes on a water bath, during which a solid begins to precipitate out. The mixture is cooled, and the precipitate obtained is filtered and recrystallized in ethanol/water, 55 g (Yield 72%) of a solid having an m.p. of 190°–193° C., which is morpholine N,N,O-triacetyl-1-amino-2-naphthol-4-sulphonate, being obtained. The IR spectrum (KBr) has the following bands: 3,000; 2,810; 2,520; 1,760; 1,720; 1,690; 1,360; 1,230; 1,100; 1,050; 770; 620.

NMR (DMSO $d_6$) δ 8.9–7.4 (m, aromatic), δ 3.1

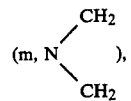

δ 3.8

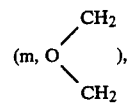

δ 2.4 (s, $-OCOCH_3$), δ 2.3 (s, $CH_3-CO-N-COCH_3$).

EXAMPLE 3

A mixture of 12.3 g (0.05 mole) of 1-amino-2-naphthol-4-sulphonic acid, 7.5 ml of pyridine and 15.5 ml of acetic anhydride is heated until the components have fully dissolved and is then left to cool, following which 5 ml of absolute ethanol is added. The precipitate obtained is filtered, and when dry is recrystallized in 95% ethanol to give 13.3 g (Yield 64.3%) of pyridine N,O-diacetyl-1-amino-2-naphthol-4-sulphonate which melts at 194°–196° C. The IR spectrum (KBr) has the following bands: 3,220; 1,750; 1,680; 1,500; 1,200; 1,150; 750; 640. NMR (DMSO $d_6$) $\delta$ 9.1–7.5 (m, aromatic), $\delta$ 2.6 (s, O—CO—$CH_3$), $\delta$ 2.5 (s, N—CO—$CH_3$).

EXAMPLE 4

50 g (0.14 mole) of potassium N,N,O-triacetyl-1-amino-2-napthol-4-sulphonate and 100 ml of ethanol are placed in a 500 ml flask provided with a stirrer and a reflux condenser, and the resultant suspension is heated to boiling, distilled water being added until the components have completely dissolved. A solution formed from 24.5 (0.13 mole) of sodium bitartrate monohydrate in 140 ml of water is then added, a precipitate corresponding to potassium bitartrate being formed immediately. The suspension is stirred and heated at 50° C. for one hour and is then cooled to 0° C. The cold suspension is filtered, and the filtrate is evaporated to dryness to give a residue which is recrystallized in ethanol/water, resulting in sodium N,N,O-triacetyl-1-amino-2-naphthol-4-sulphonate, which has a m.p. above 300° C. and whose IR spectrum (KBr) has the following bands: 3,475; 1,765; 1,725; 1,695; 1,375; 1,200; 1,050; 1,025; 770; 710; 630.

EXAMPLE 5

30 g (0.077 mole) of sodium N,N,O-triacetyl-1-amino-2-naphthol-4-sulphonate and 100 ml of distilled water are placed in a 250 ml flask provided with a stirrer and reflux condenser. The resultant solution is heated under reflux for 3 hours. After refluxing, the reaction mixture is evaporated to dryness under a low vacuum in a rotary evaporator. The residue obtained is recrystallized in methanol to give 24 g (Yield 89.7%) of sodium N,O-diacetyl-1-amino-2-naphthol-4-sulphonate, whose m.p. is 244°–246° C. and whose IR spectrum (KBr) has the following bands: 3,275; 1,765; 1,670; 1,545; 1,400; 1,240; 1,220; 1,200; 1,060; 790; 665.

EXAMPLE 6

A mixture formed from 12 g (0.05 mole) of 1-amino-2-naphthol-4-sulphonic acid, 7.2 ml of pyridine, 12 ml of acetic acid and 4.5 ml of acetic anhydride is heated while stirring until the components have completely dissolved. 15 ml of ethyl alcohol is added to the solution and the precipitate obtained on cooling is collected in a filter, to give 17 g (Yield 94%) of pyridine N-acetyl-1-amino-2-naphthol-4-sulphonate having an m.p. of 210°–215° C. The compound has a characteristic IR spectrum.

EXAMPLE 7

10 g (0.02 mole) of pyridine N-acetyl-1-amino-2-naphthol-4-sulphonate is dissolved in the minimum amount of boiling water and 3.42 g (0.02 mole) of morpholine hydrochloride is added to this solution. After heating on a water bath for 15 minutes, the solution is cooled to 3° C. and 6 g (Yield 58.8%) of morpholine N-acetyl-1-amino-2-naphthol-4-sulphonate is finally obtained, which has a m.p. of 202°–204° C. The IR spectrum (KBr) has the following bands: 3,240; 3,000; 2,850; 2,500; 1,650; 1,530; 1,385; 1,290; 1,200; 1,110; 1,050; 755; 645.

This compound may also be obtained in the following way: 24.7 g (0.06 mole) of pyridine N,O-diacetyl-1-amino-2-naphthol-4-sulphonate, 2.13 g (0.24 mole) of morpholine and 150 ml of ethanol are placed in a flask provided with a stirrer and a heater. The mixture is refluxed for 90 minutes, during which it evaporates to dryness. The residue obtained is washed with ether and recrystallized in ethanol, 14.1 g (Yield 62.3%) of morpholine N-acetyl-1-amino-2-naphthol-4-sulphonate being obtained, having identical characteristics to those described above in this example.

EXAMPLE 8

12 g (0.05 mole) of 1-amino-4-naphthalenesulphonic acid, 7.2 ml of pyridine and 15 ml of acetic anhydride are placed in a flask provided with a stirrer and heater. The mixture is heated until the solution is clear, at which point 10 ml of absolute ethanol is added and the mixture is allowed to cool, first to ambient temperature and then in a refrigerator to 3° C. for 3 hours. The precipitate obtained is collected in a filter and is recrystallized in ethanol to give 11 g (Yield 59.4%) of pyridine N-acetyl-1-aminonaphthalene-4-sulphonate, having a m.p. of 172°–175° C. and whose IR spectrum (KBr) has the following bands: 3,400; 3,220; 1,640; 1,525; 1,370; 1,325; 1,200; 1,030; 850; 675; 635.

EXAMPLE 9

15 g (0.04 mole) of pyridine N-acetyl-1-aminonaphthalene-4-sulphonate is dissolved in the minimum amount of water in an Erlenmeyer flask. This solution is conveniently cooled and is acidified with concentrated hydrochloric acid, following which the precipitate formed is collected in a filter to give N-acetyl-1-amino-4-naphthalenesulphonic acid, which is then filtered, washed and dried, and suspended in water. An aqueous solution of the stoichiometric amount of tranexamic acid (AMCHA) is then added, and the mixture is stirred for 15 minutes at ambient temperature and evaporated to dryness. The residue obtained is recrystallized in absolute alcohol, 14.1 g (Yield 76.6%) of AMCHA N-acetyl-1-aminonaphthalene-4-sulphonate finally being obtained, whose m.p. is 214°–215° C. and whose IR spectrum (KBr) has the following bands: 1,670; 1,650; 1,530; 1,510; 1,370; 1,320; 1,200; 1,040; 750; 670; 640.

EXAMPLE 10

12.5 g (0.03 mole) of pyridine N-acetyl-1-aminonaphthalene-4-sulphonate is dissolved in the minimum amount of hot water in a flask provided with a stirrer. 8.9 g (0.07 mole) of morpholine hydrochloride dissolved in water is added to this solution and the resultant mixture is stirred for 15 minutes on a water bath, following which it is cooled in a refrigerator and the solid precipitate formed is collected in a filter. The precipitate is dried and recrystallized in ethanol/water, 10.8 g (Yield 85%) of a solid melting at 225°–228° C. being obtained. This compound is morpholine N-acetyl-1-aminonaphthalene-4-sulphonate, whose IR spectrum (KBr) has the following bands: 3,275; 3,200, 3,000, 2,800, 2,300; 1,690; 1,530; 1,200; 1,160; 1,100; 1,040; 765; 680; 640.

EXAMPLE 11

40 g (0.11 mole) of potassium N,N,O-triacetyl-1-amino-2-naphthol-4-sulphonate is dissolved in the minimum amount of water in an Erlenmeyer flask provided with a stirrer. 21.4 g (0.11 mole) of tranexamic acid (AMCHA) hydrochloride is added to this solution. The resultant mixture is carefully heated while stirring continuously, and a precipitate then appears which redissolves as heating is continued. The solution is cooled and the precipitate obtained, which weighs 49 g (Yield 83%) and has an m.p. of 186°–189° C., is collected on a filter. This compound is AMCHA N,N,O-triacetyl-1-amino-2-naphthol-4-sulphonate whose IR spectrum (KBr) has the following bands: 3,020; 2,970; 1,760; 1,720; 1,690; 1,500; 1,350; 1,200; 1,040; 1,000; 760; 610.

NMR (DMSO $d_6$) δ 9.1–7.5 (m, aromatic) δ 2.1 (s, OCOCH$_3$) δ 2.5 (s, CH$_3$CONCOCH$_3$) δ 2.4–1.1 (m, cyclohexyl).

EXAMPLE 12

This example concerns the preparation of various pharmaceutical compositions containing as active principle, the compound sodium N,O-diacetyl-1-amino-2-naphthol-4-sulphonate obtained according to Example 5.

(a) 1000 no. 0 gelatin capsules are produced, each one containing 250 mg of the compound (Example 5).

The composition is as follows:

| For 1000 capsules | |
|---|---|
| Compound (Example 5) | 250 g |
| Lactose | 75 g |
| Microcrystalline cellulose | 80 g |
| Magnesium stearate | 100 g |

The components are first screened and are then mixed until homogeneous and the resultant powder is added to the gelatin capsules by means of a suitable filling device.

(b) 10,000 tablets are produced, each one containing 250 mg of the compound (Example 5).

The composition is as follows:

| For 10,000 tablets | |
|---|---|
| Compound (Example 5) | 2,500 g |
| Microcrystalline cellulose | 1,270 g |
| Lactose | 1,000 g |
| Plasdone (polyvinylpyrrolidone) | 80 g |
| Primogel | 100 g |
| Magnesium stearate | 50 g |

The compound (Example 5) is mixed with the lactose and half the Primogel. The resultant mixture is then kneaded with a 20% aqueous solution of Plasdone, screened through a 30-mesh sieve, and dried at 60° C. for 10 hours. The dried granulate is screened through a 30-mesh sieve. The remaining half of the Primogel, the microcrystalline cellulose and the magnesium stearate are then added to this mixture. After being homogenized, the mixture is compressed in a suitable pressing machine.

(c) 100 liters of oral suspension containing 500 mg of the compound (Example 5) for each 5 ml dose are prepared.

The suspension has the following composition:

| For 100 liters | |
|---|---|
| Compound (Example 5) | 10,000 g |
| Sorbitol 70% U.S.P. (United States Pharmacopoeia) | 25,000 g |
| Carboxymethylcellulose | 1,000 g |
| Glycerine U.S.P. | 10,000 g |
| Nipagin | 120 g |
| Nipasol | 30 g |
| Polysorbate 80 U.S.P. | 100 g |
| Avicel RC-591 | 1,500 g |
| Sweeteners and flavourings | ad lib. |
| Distilled water, to make up to | 100 l |

The sorbitol, glycerine, polysorbate 80, Nipagin and Nipasol are mixed while heating until the last two of the afore-mentioned substances have dissolved. The compound (Example 5) is dispersed in the mixture and homogenized with a turbostirrer. The carboxymethylcellulose and Avicel RC-591 are suspended in part of the water and combined with the preceding mixture; finally, the sweeteners and aromas or flavourings are added and the whole is made up to 100 liters.

(d) 100 liters of oral solution containing 500 mg of compound (Example 5) for each 5 ml dose are produced.

The composition of the solution is as follows:

| For 100 liters | |
|---|---|
| Compound (Example 5) | 10,000 g |
| Sorbitol 70% U.S.P. | 25,000 g |
| Glycerine U.S.P. | 10,000 g |
| Nipagin | 120 g |
| Nipasol | 30 g |
| Sweeteners and fragrances/flavourings | ad lib. |
| Distilled water, to make up to | 100 l |

The sorbitol, glycerine, Nipagin and Nipasol are mixed, the mixture being heated until the last two substances have dissolved. Finally, the compound (Example 5) and the sweeteners and fragrances are added and the whole solution is made up to 100 liters by adding the distilled water.

(e) 10 liters of injectable solution containing 250 mg of compound (Example 5) per 5 ml are produced.

The composition of the solution is as follows:

| For 10 liters | |
|---|---|
| Compound (Example 5) | 500 g |
| Water for injection | 10 l |

The compound (Example 5) is dissolved in water and made up to 10 liters. The solution is passed through a 0.22 μm filter and metered in 5 ml doses in a suitable injection solution filling machine.

EXAMPLE 13

The pharmaceutical compositions of Example 12 are prepared in a similar manner from the corresponding compounds of the previous examples, especially Examples 1, 2, 4 and 11.

Pharmacological description

The compounds embodying the invention are of low toxicity, mainly have a hemostatic and antifibrinolytic activity, and act on the capillary permeability and resistance.

Hemostatic activity

The hemostatic activity is determined by means of a quantitative study of the mean bleeding (clotting) time measured in a rabbit ear by the technique described by Roskam and Pauwen.

Ethamsylate was used as a standard, and the results obtained were as follows:

| Product of | Dose mg/kg | Route | % Effect |
|---|---|---|---|
| Example 1 | 10 | i.v. | 18.2 |
|  | 100 | i.v. | 23 |
| Example 2 | 10 | i.v. | 24.7 |
|  | 100 | i.v. | 13 |
| Example 4 | 10 | i.v. | 29.7 |
|  | 100 | i.v. | 29.8 |
| Example 5 | 25 | i.v. | 10.6 |
| Example 11 | 10 | i.v. | 20 |
|  | 100 | i.v. | 32 |
| AMCHA | 10 | i.v. | 22.5 |
|  | 100 | i.v. | 26.5 |
| Ethamsylate | 10 | i.v. | 22.11 |

Antifibrinolytic activity

The antifibrinolytic activity is evaluated "in vitro" by means of fibrin plates according to the modified and standardized method of Astrup and Mullertz.

The antifibrinolytic activity of the test solution is calculated by interpolating the lysis response in a dose/response curve obtained with reference solutions (graduated dilutions of a standard enzyme). AMCHA was used as a standard antifibrinolytic compound.

The results obtained are as follows:

| Product of | Relative capacity | Weight capacity |
|---|---|---|
| Example 1 | 2.06 | 0.91 |
| Example 2 | 1.67 | 0.59 |
| Example 4 | 2.61 | 1.21 |
| Example 5 | 1.19 | 0.55 |
| Example 11 | 3.36 | 1.19 |
| AMCHA | 1 | 1 |
| Ethamsylate | 0.47 | 0.28 |

Capillary permeability

The effect on the capillary permeability is determined by means of Lefebre's method, which is based on measuring, at the time of appearance of a coloration, the vascular permeability produced by histamine in rats that have been injected with the product under investigation.

Ethamsylate is used as a standard, and the results obtained are as follows:

| Product of | Route | Dose g/kg | % Effect |
|---|---|---|---|
| Example 1 | Subcutaneous | 0.100 | 19 |
| Example 2 | " | 0.100 | 29 |
| Example 11 | " | 0.100 | 14 |
| AMCHA | " | 0.100 | −2 |
| Ethamsylate | " | 0.100 | 26.33 |

Capillary resistance

The effect on the capillary resistance is determined by means of a modified technique based on that of Lavollay. An increasingly powerful vacuum is applied to the skin, and the time that elapses before the first central petechiae appear is taken as a measure of the capillary resistance. Three batches of guinea-pigs are used for each product tested, one batch being a normal batch and the two other batches being subjected to a scorbutic diet, one of the latter batches having received the product under investigation from the start of the trial. An initial basal reading and other weekly readings are taken for four weeks. Ethamsylate is used as a standard. The results obtained are as follows:

| Product of | Route | Dose g/kg | % Effect |
|---|---|---|---|
| Example 1 | Oral | 0.175 | 23.6 |
| Example 2 | " | 0.175 | 23.95 |
| Example 4 | " | 0.175 | 17.9 |
| Example 5 | " | 0.175 | 26 |
| Example 11 | " | 0.175 | 22.6 |
| AMCHA | " | 0.175 | 20.08 |
| Ethamsylate | " | 0.175 | 14.18 |

Acute toxicity

The $LD_{50}$ in mice is determined for the endovenous, intraperitoneal and oral routes. The results obtained are as follows:

| Product of | Acute toxicity g/kg I.v. route | I.p. route | Oral route |
|---|---|---|---|
| Example 1 | 0.653 | 3.56 | >7 |
| Example 2 | 1.53 | 4.04 | >7 |
| Example 4 | 3.51 | 5.26 | >7 |
| AMCHA | 1.6 | 4.2 | >15 |
| Ethamsylate | 0.8 | — | — |

We claim:

1. A compound selected from the group consisting of naphthalenesulphonic acid derivatives of the formula:

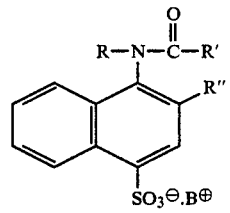

wherein R is hydrogen or a lower alkanoyl radical, R' is a lower alkyl radical, R" is hydroxy or a lower alkanoyloxy radical, and B+ is a cation of a compound that contains a basic nitrogen atom selected from the group consisting of tranexamic acid, ε-aminocaproic acid and p-aminomethylbenzoic acid.

2. A compound according to claim 1 wherein R is hydrogen or acetyl; R' is methyl; R" is hydroxy or acetyloxy; and B+ is the cation of tranexamic acid.

3. A compound according to claim 1 wherein R is acetyl; R' is methyl; R" is acetyloxy; and B+ is the cation of tranexamic acid.

4. A pharmaceutical composition having an action as haemostatic and antifibrinolytic activity and acting on the capillary permeability and resistance, said composition comprising a pharmaceutically acceptable carrier and said action effective amount of the compound of claim 1.

5. Composition according to claim 4, wherein the pharmaceutically acceptable carrier is adapted for oral administration.

6. Composition according to claim 4, wherein the pharmaceutically acceptable carrier is adapted for parenteral administration.

7. Composition according to claim 4, wherein the pharmaceutically acceptable carrier is adapted for topical application.

* * * * *